United States Patent
O'Lenick

(10) Patent No.: US 9,186,311 B1
(45) Date of Patent: Nov. 17, 2015

(54) GLYCERIN POLYSILICONES

(71) Applicant: Thomas George O'Lenick, Dacula, GA (US)

(72) Inventor: Thomas George O'Lenick, Dacula, GA (US)

(73) Assignee: Surfa Tech Corporation, Lawrenceville, GA (US)

( * ) Notice: Subject to any disclaimer, the term of this patent is extended or adjusted under 35 U.S.C. 154(b) by 21 days.

(21) Appl. No.: 13/998,176

(22) Filed: Oct. 9, 2013

Related U.S. Application Data

(60) Provisional application No. 61/958,903, filed on Aug. 9, 2013.

(51) Int. Cl.
*A01N 37/02* (2006.01)
*A01N 37/06* (2006.01)
*A61K 31/225* (2006.01)
*A01N 25/00* (2006.01)
*A61K 47/00* (2006.01)
*A61K 8/58* (2006.01)
*A61Q 19/00* (2006.01)

(52) U.S. Cl.
CPC .............. *A61K 8/585* (2013.01); *A61Q 19/007* (2013.01)

(58) Field of Classification Search
None
See application file for complete search history.

*Primary Examiner* — Craig Ricci
*Assistant Examiner* — Jared D Barsky

(57) ABSTRACT

The present invention is directed to a series of glycerin polysilicones. By glycerin polysilicones in meant polymers that have silicone portions that are functionalized with glycerin groups. The polymers of the present invention can range from relatively low molecular weight (around 600 daltons) to higher molecular weight (of about 2,500 daltons). The presence of the glyceryl groups together with the silicone groups allows for the preparation of molecules uniquely suited to personal care applications, more specifically, skin care products.

9 Claims, No Drawings

GLYCERIN POLYSILICONES

RELATED APPLICATION

This application claims priority to and benefit of U.S. Provisional Application No. 61/742,504 filed Aug. 13, 2013, the disclosure of which is incorporated herein for all purposes.

1. Field of the Invention

The present invention is directed to a series of glycerin polysilicones. By glycerin polysilicones in meant polymers that have silicone portions that are functionalized with glycerin groups. The polymers of the present invention can range from relatively low molecular weight (around 600 daltons) to higher molecular weight (of about 2,500 daltons). The presence of the glyceryl groups together with the silicone groups allows for the preparation of molecules uniquely suited to personal care applications, more specifically, skin care products.

The lower molecular weight products are good wetting agents, providing for improved spreadability of oily phases. The surface tension of the oil is generally reduced from around 32 dynes/cm to around 25 dynes/cm.

Higher molecular weight products will have better film forming properties and improved skin feel.

2. Background of the Invention

Silicone polymers have been used in personal care applications for many years. One approach to treating skin is to apply a hydrophobic, greasy coating to the skin, which keeps moisture from evaporating from the skin. These silicone polymers, often refereed to as silicone fluids, find use in a variety of cosmetic formulations. Diana Steinmetz on wikianswers.com states: Dimethicone is an excellent skin care product but whether it is right for you depends on what you are looking for. It is a type of silicone oil. Silicone oils in general add glide and smooth properties to skin care products. Dimethicones are unmodified silicone oils. Unmodified silicone oils stay on the surface of the skin, as the molecules are too large to penetrate deeply into the skin. Because it stays on the surface of the skin, dimethicone provides a skin barrier. This is an excellent ingredient for someone whose skin barrier has been disrupted by a laser treatment (apply immediately after treatment and daily for at least one week afterwards) or whose skin barrier is seriously compromised, such as someone with rosacea whose epidermis is thin and needs added protection. Dimethicone will help take over some of the normal functions of the skin barrier, such as preventing transdermal water loss. It is a good product to use in dry, hot climates. Dimethicone used in hair products coats the hair.

Skin protectants are considered drugs and are controlled by the FDA. They generally contain around 20% by weight of 350 viscosity dimethicone. This class of product (1) temporarily protects and helps relieve chapped or cracked skin; (2) helps protect from the drying effects of wind and cold weather; (3) helps treat and prevent diaper rash and (4) protects minor skin irritation due to diaper rash and helps seal out wetness.

U.S. Pat. No. 4,996,238 issued Feb. 26, 1991 to Matravers discloses a Method of treating diaper rash. Specifically it discloses A skin protective composition for exhibiting enhanced water repellency and conditioning effects containing aliphatic waxes and hydrophobic silicones in a nonallergenic, non-toxic, cosmetically acceptable carrier. The composition is useful to protect mammals from solar radiation and in the treatment of diaper rash. This patent clearly points out the hydrophobic nature of silicones applied to skin. They are greasy and prevent water penetration.

Another approach is to treat the skin with compounds that attract moisture to the skin thereby improving moistruization. U.S. Pat. No. 5,411,729 to O'Lenick issued May 2, 1995 entitled "Silicone polyester polymers as durable humectants" discloses novel series of silicone polyesters, which are useful as humectants for softening, conditioning and lubricating hair and skin. Compounds of the invention by are prepared by the esterification of (a) a hydroxyl containing silicone compound selected from silanol and dimethicone copolyol (b) a diacid and (c) a poly-hydroxy compound selected from the group consisting of glycerine, methyl glucoside, sorbitol and their alkoxylates and (d) optionally a fatty acid. The polyesters of the present invention allow for the formulation of personal care products in which the humectant is substantive to the hair and skin by virtue of the structure of the polyester and can be formulated into a variety of products for delivery to hair and skin. The O'Lenick patent teaches "We have discovered that the incorporation of a compound selected from the group consisting of glycerine, methyl glucoside, sorbitol and their alkoxylates into a silicone polyester in relatively low concentrations results in polyesters which can be made soluble in many different solvents and which give the beneficial properties of the glycerine, methyl glucoside, sorbitol and their alkoxylates and is durable to the hair and skin." This patent failed to recognize the importance of surface tension lowering to obtain a thin film and the importance of the exact structure of the polymer is to product performance.

Unlike the polymers described above the polymers of the present invention can be fine tuned to provide sections that have humectant moieties and silicone moieties that allow for a two pronged approach to moisturization and a locking in of the moisture. Further, prior to the present invention it was not recognized that surface tension lowering and it's effect on film thickness and its importance in making cosmetically elegant products for skin moisturization. Simply put the consumer does not want sticky, greasy skin moisturizers for daily use.

THE INVENTION

Objective of the Invention

It is the object of the present invention to provide a series of Glycerin Polysilicones. Glycerin Polysilicones are polymers that have silicone polymers that are functionalized with glycerin groups. The polymers of the present invention can range from relatively low molecular weight (around 600 daltons) to higher molecular weight (of about 2,500 daltons). The presence of the glyceryl groups together with the silicone groups allows for the preparation of molecules uniquely suited to personal care applications, more specifically, skin care products. The lower molecular weight products are good wetting agents, providing for improved spreadability of oily phases. The surface tension of the oil is generally reduced from around 32 dynes/cm to around 25 dynes/cm. Higher molecular weight products will have better film forming properties and improved skin feel.

All patents cited herein are incorporated by reference where appropriate, all temperatures are degrees C., all percentages are percentages by weight, unless otherwise specified.

SUMMARY OF THE INVENTION

The present invention is directed to a series of glycerin polysilicones. By glycerin polysilicones in meant polymers that have silicone portions that are functionalized with glycerin groups. The polymers of the present invention can range from relatively low molecular weight (around 600 daltons) to higher molecular weight (of about 2,500 daltons). The presence of the glyceryl groups together with the silicone groups allows for the preparation of molecules uniquely suited to personal care applications, more specifically, skin care products. The lower molecular weight products are good wetting agents, providing for improved spreadability of oily phases. The surface tension of the oil is generally reduced from around 32 dynes/cm to around 25 dynes/cm. Higher molecular weight products will have better film forming properties and improved skin feel.

DETAILED DESCRIPTION OF THE INVENTION

Glycerin Polysilicones
The polysilicones of the present invention have the following structure;

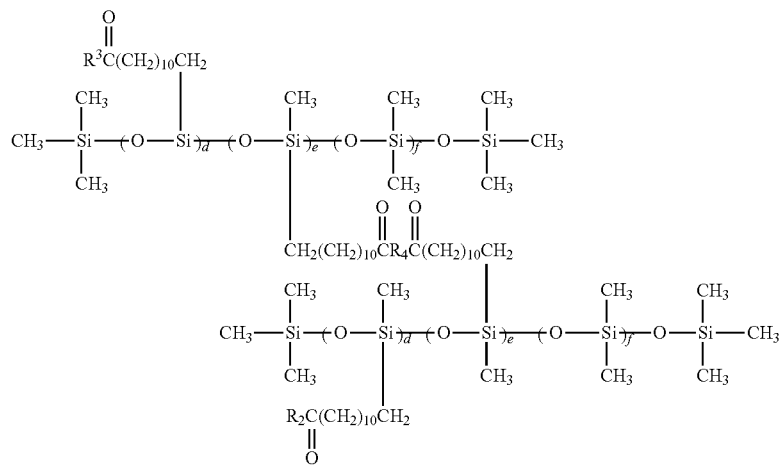

wherein;

d is an integer ranging from 1 to 10;

e is an integer ranging from 0 to 4;

f is an integer ranging from 0 to 20;

c is an integer ranging from 3 to 30, with the proviso that d+e+f=c;

$R^3$ is selected from the group consisting of:

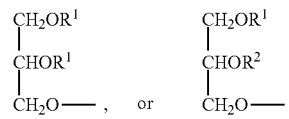

and mixtures thereof.
wherein;
$R^1$ conforms to the following structure:

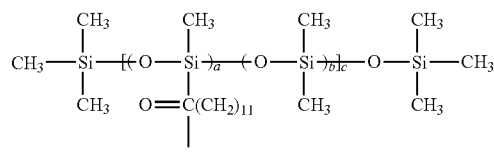

a is an integer ranging from 1 to 10;
b is an integer ranging from 0 to 20;
$R^2$ is alkyl containing 8 to 26 carbons;
$R^4$ conforms to the following structure:

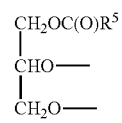

wherein;
$R^5$ is selected from a group consisting of:

$$CH_3-\underset{CH_3}{\underset{|}{Si}}-\underset{}{\overset{}{(\!(}}O-\underset{CH_3}{\underset{|}{Si}}\underset{}{\overset{}{)_a}}\underset{}{\overset{}{(\!(}}O-\underset{O=C(CH_2)_{11}}{\underset{|}{Si}}\underset{}{\overset{}{)_bc}}-O-\underset{CH_3}{\underset{|}{\overset{CH_3}{\overset{|}{Si}}}}-CH_3 \text{ and}$$

alkyl containing 8 to 26 carbons;
a is an integer ranging from 1 to 10;
b is an integer ranging from 0 to 20.

Glycereth Polysilicones

The polysilicones of the present invention have the following structure;

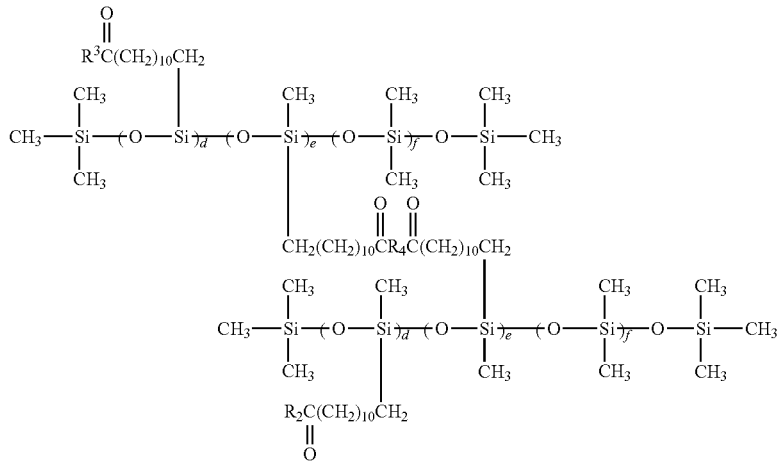

wherein;

d is an integer ranging from 1 to 10;

e is an integer ranging from 0 to 4;

f is an integer ranging from 0 to 20;

c is an integer ranging from 3 to 30, with the proviso that d+e+f=c;

$R^2$ is alkyl containing 8 to 26 carbons.

$R^3$ is selected from the group consisting of:

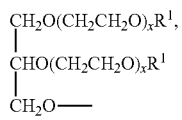 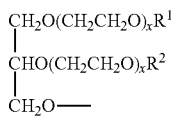

and mixtures thereof.

wherein;

x is an integer ranging from 3 to 8.

$R^1$ is selected from a silicone polymer that has the following structure:

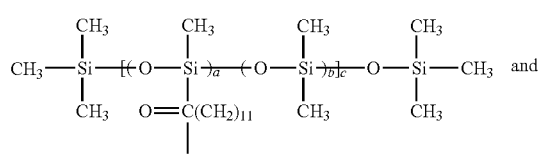

alkyl ranging from 8 to 26 carbons, or mixtures thereof. With the proviso that $R^1$ is different than $R^2$;

a is an integer ranging from 1 to 10;

b is an integer ranging from 0 to 20;

$R^4$ conforms to the following structure:

$$\begin{array}{c} CH_2O(CH_2CH_2O)_xR^5 \\ | \\ CHO(CH_2CH_2O)_x- \\ | \\ CH_2O(CH_2CH_2O)_x- \end{array}$$

wherein;

x is an integer ranging from 3 to 8;

$R^5$ is selected from a group consisting of:

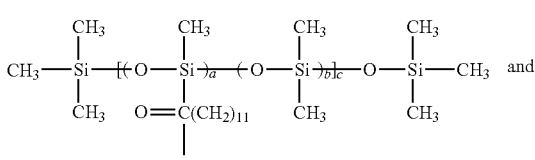

alkyl containing 8 to 26 carbons;

a is an integer ranging from 1 to 10;

b is an integer ranging from 0 to 20.

Glycerin Polysilicones Applied to Skin

Another aspect of the present invention is a process for moisturizing skin, which comprises contacting the skin with an effective moisturizing concentration of a polysilicone having the following structure;

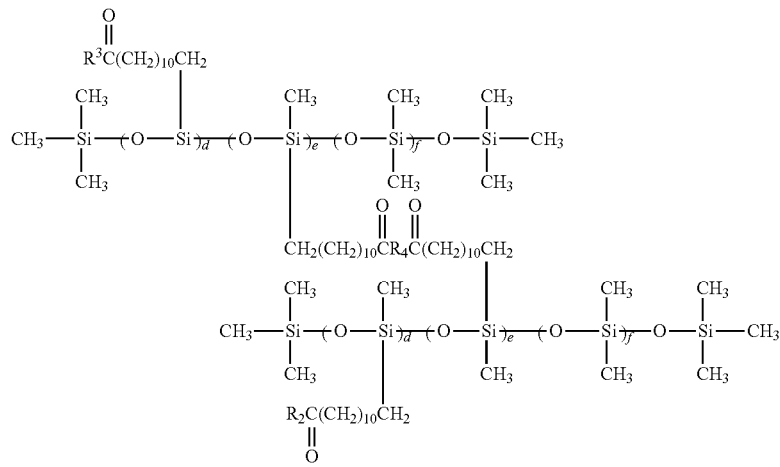

wherein;
d is an integer ranging from 1 to 10;
e is an integer ranging from 0 to 4;
f is an integer ranging from 0 to 20;
c is an integer ranging from 3 to 30, with the proviso that d+e+f=c;
$R^3$ is selected from the group consisting of:

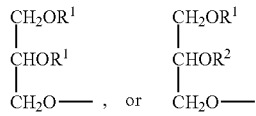

and mixtures thereof.
wherein;
$R^1$ conforms to the following structure:

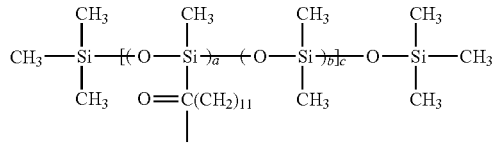

a is an integer ranging from 1 to 10;
b is an integer ranging from 0 to 20;
$R^2$ is alkyl containing 8 to 26 carbons;

$R^4$ conforms to the following structure:

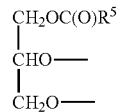

wherein;
$R^5$ is selected from a group consisting of:

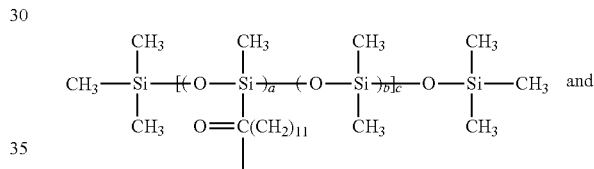

and alkyl containing 8 to 26 carbons;
a is an integer ranging from 1 to 10;
b is an integer ranging from 0 to 20.

Glycereth Polysilicones

Still another aspect of the present invention is a process for moisturizing skin which comprises contacting the skin with an effective moisturizing concentration of a polysilicone having the following structure;

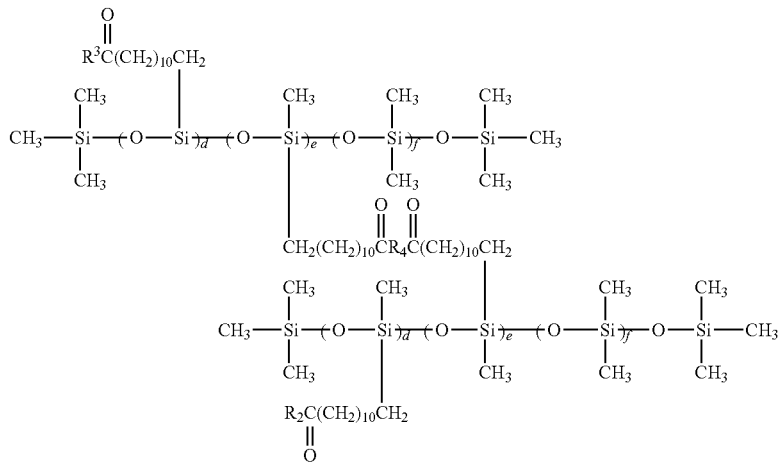

wherein;
d is an integer ranging from 1 to 10;
e is an integer ranging from 0 to 4;
f is an integer ranging from 0 to 20;
c is an integer ranging from 3 to 30, with the proviso that d+e+f=c;
$R^2$ is alkyl containing 8 to 26 carbons.
$R^3$ is selected from the group consisting of:

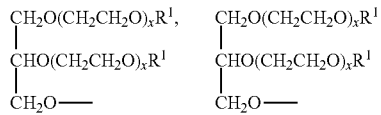

and mixtures thereof.
wherein;
x is an integer ranging from 3 to 8.
$R^1$ is selected from a silicone polymer that has the following structure:

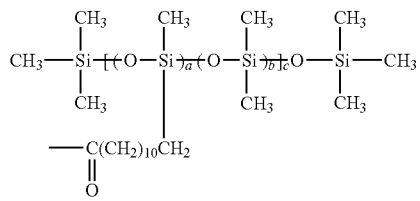

, and
alkyl ranging from 8 to 26 carbons, or mixtures thereof, with the proviso that $R^1$ is different than $R^2$;
a is an integer ranging from 1 to 10;
b is an integer ranging from 0 to 20;
$R^4$ conforms to the following structure:

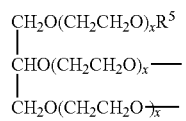

wherein;
x is an integer ranging from 3 to 8;
$R^5$ is selected from a group consisting of:

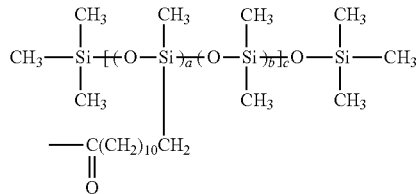

and
alkyl containing 8 to 26 carbons;
a is an integer ranging from 1 to 10;
b is an integer ranging from 0 to 20.
Preferred Embodiments
In a preferred embodiment, a is 1.
In a preferred embodiment, a is 5.
In a preferred embodiment, a is 10.
In a preferred embodiment, b is 0.
In a preferred embodiment, b is 5.
In a preferred embodiment, b is 10.
In a preferred embodiment x is 3.
In a preferred embodiment x is 8.
In a preferred embodiment $R^2$ is alkyl containing 8 carbons.
In a preferred embodiment $R^2$ is alkyl containing 12 carbons.
In a preferred embodiment $R^2$ is alkyl containing 16 carbons.
In a preferred embodiment $R^2$ is alkyl containing 18 carbons.
In a preferred embodiment $R^2$ is alkyl containing 20 carbons.
In a preferred embodiment $R^2$ is alkyl containing 22 carbons.
In a preferred embodiment $R^2$ is alkyl containing 24 carbons.
In a preferred embodiment $R^2$ is alkyl containing 26 carbons.
In a preferred embodiment $R^5$ is

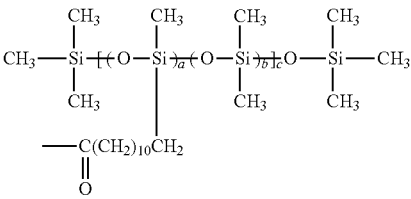

In a preferred embodiment $R^5$ is alkyl containing 8 to 26 carbons.
In a preferred embodiment d is 1.
In a preferred embodiment said effective conditioning concentration ranges from 0.5 to 15% by weight.

Raw Materials

Fatty Acids
Fatty acids useful in the practice of the present invention are items of commerce commercially available from Cognis.
Fatty Acids
Fatty acids useful as raw materials in the preparation of compounds of the present invention are commercially available from a variety of sources including Procter and Gamble of Cincinnati Ohio. The structures are well known to those skilled in the art.

| Saturated | | | |
|---|---|---|---|
| Example | R Formula | Common Name | Molecular Weight |
| 1 | $C_7H_5$ | Caprylic | 144 |
| 2 | $C_9H_{19}$ | Capric | 172 |
| 3 | $C_{11}H_{23}$ | Lauric | 200 |
| 4 | $C_{13}H_{27}$ | Myristic | 228 |
| 5 | $C_{14}H_{29}$ | Pentadecanoic | 242 |
| 6 | $C_{15}H_{31}$ | Palmitic | 256 |
| 7 | $C_{17}H_{35}$ | Stearic | 284 |
| 8 | $C_{17}H_{35}$ | Isosteric | 284 |
| 9 | $C_{19}H_{39}$ | Arachidinic | 312 |
| 10 | $C_{21}H_{43}$ | Behenic | 340 |
| 12 | $C_{26}H_{53}$ | cetrotic | 396 |
| 13 | $C_{33}H_{67}$ | geddic acid | 508 |

| Unsaturated | | | |
|---|---|---|---|
| Example | R Formula | Common Name | Molecular Weight |
| 14 | $C_{17}H_{33}$ | Oleic | 282 |
| 15 | $C_{17}H_{31}$ | Linoleic | 280 |
| 16 | $C_{17}H_{29}$ | Linolenic | 278 |
| 17 | $C_{15}H_{29}$ | Palmitoleic | 254 |
| 18 | $C_{13}H_{25}$ | Myristicoleic | 226 |
| 19 | $C_{21}H_{41}$ | Erucic | 338 |

Glycerin

Glycerin is an item of commerce and is available from a variety of sources including Cognis of Cincinnati Ohio. It conforms to the following structure:

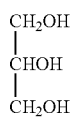

Glycerin is propane-1,2,3-triol and has a CAS number of 56-81-5.

Silicone Undecylenates

Silicone undecylenates are sold commercially by Siltech L.L.C. under the name Silmer UME. They are items of commerce and have following structure:

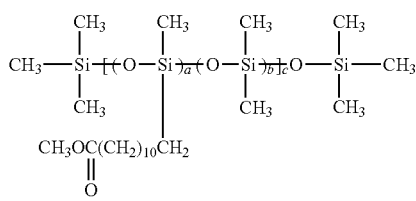

| Example | a | B | c | Molecular Weight |
|---|---|---|---|---|
| 20 | 1 | 2 | 3 | 566 |
| 21 | 4 | 0 | 4 | 1234 |
| 22 | 10 | 20 | 30 | 4346 |

Glycereth Compounds

Glycereth compounds is commercially available from Abeitec Corporation, and have the following structure:

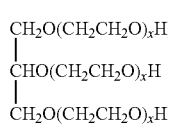

wherein;

x is an integer ranging from 1 to 10.

| Example | X | Molecular Weight |
|---|---|---|
| 23 | 1 | 224 |
| 24 | 3 | 488 |
| 25 | 8 | 1,148 |
| 26 | 10 | 1,412 |

General Procedure

Glycerin Mono-esters

A specified number of grams of glycerin are added to a specified amount of fatty acids (Examples 1-19) or Silmer UME (Example 20). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

| | Glycerin | $R^1$ | |
|---|---|---|---|
| Example | Grams | Example | Grams |
| 27 | 35.0 | 20 | 215.0 |
| 28 | 87.2 | 2 | 162.8 |
| 29 | 61.2 | 7 | 188.8 |
| 30 | 61.2 | 8 | 188.8 |
| 31 | 53.3 | 10 | 196.7 |
| 32 | 61.5 | 14 | 188.5 |

Glycerin Di-esters

A specified number of grams of glycerin are added to a specified amount of fatty acids (examples 1-19) and/or Silmer UME (example 20). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

| | Glycerin | $R^1$ | | $R^2$ | |
|---|---|---|---|---|---|
| Example | Grams | Example | Grams | Example | Grams |
| 33 | 28.1 | 20 | 169.5 | 2 | 52.4 |
| 34 | 23.1 | 20 | 141.8 | 10 | 85.2 |
| 35 | 19.0 | 20 | 114.5 | 20 | 116.5 |
| 36 | 34.9 | 8 | 107.6 | 7 | 107.6 |
| 37 | 42.0 | 8 | 129.5 | 2 | 78.5 |
| 38 | 32.2 | 10 | 119.0 | 14 | 98.7 |

Glycereth Mono-esters

A specified number of grams of glycereth (examples 23-26) are added to a specified amount of fatty acids (Examples 1-19) or Silmer UME (Example 20). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

|         | Glycereth |       | R¹      |       |
|---------|-----------|-------|---------|-------|
| Example | Example   | Grams | Example | Grams |
| 39      | 23        | 71.8  | 20      | 178.2 |
| 40      | 24        | 184.8 | 2       | 65.2  |
| 41      | 25        | 200.4 | 7       | 49.6  |
| 42      | 26        | 208.1 | 8       | 41.9  |
| 43      | 23        | 99.3  | 10      | 150.7 |
| 44      | 25        | 200.7 | 14      | 49.3  |

Glycereth Di-esters

A specified number of grams of glycereth (examples 23-26) are added to a specified amount of fatty acids (examples 1-19) and/or Silmer UME (example 20). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

|         | Glycereth |       | R¹      |       | R²      |       |
|---------|-----------|-------|---------|-------|---------|-------|
| Example | Example   | Grams | Example | Grams | Example | Grams |
| 45      | 25        | 152.2 | 20      | 75.0  | 2       | 22.8  |
| 46      | 25        | 139.7 | 20      | 68.9  | 10      | 41.4  |
| 47      | 25        | 125.9 | 20      | 62.1  | 20      | 62.1  |
| 48      | 26        | 178.3 | 8       | 35.9  | 7       | 35.9  |
| 49      | 23        | 32.2  | 8       | 119.0 | 2       | 98.7  |
| 50      | 24        | 109.9 | 10      | 76.6  | 14      | 63.5  |

Silicone Glycerin

A specified number of grams of Silicone Undecylenate (Examples 20-22) are added to a specified amount of glycerin diesters (Examples 31-41) and/or glycerin monoesters (examples 23-30). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

|         | Silicone Undecylenate |       | Glycerin Diester |       | Glycerin Monoester |       |
|---------|-----------------------|-------|------------------|-------|--------------------|-------|
| Example | Example               | Grams | Example          | Grams | Example            | Grams |
| 51      | 20                    | 105.0 | 45               | 145.0 | —                  | —     |
| 52      | 21                    | 61.4  | 46               | 188.6 | —                  | —     |
| 53      | 22                    | 68.1  | 47               | 181.9 | —                  | —     |
| 54      | 20                    | 118.9 | 48               | 131.1 | —                  | —     |
| 55      | 21                    | 93.9  | 49               | 156.1 | —                  | —     |
| 56      | 22                    | 97.7  | 50               | 152.3 | —                  | —     |
| 57      | 21                    | 73.4  | 45               | 139.4 | 39                 | 37.2  |
| 58      | 22                    | 87.5  | 46               | 152.7 | 40                 | 9.9   |
| 59      | 22                    | 98.6  | 46               | 129.1 | 40                 | 22.2  |
| 60      | 21                    | 60.8  | 47               | 171.6 | 41                 | 17.6  |
| 61      | 22                    | 108.1 | 48               | 124.2 | 42                 | 17.8  |
| 62      | 22                    | 114.2 | 48               | 98.3  | 42                 | 37.5  |
| 63      | 21                    | 96.8  | 49               | 120.8 | 43                 | 32.4  |
| 64      | 22                    | 103.7 | 50               | 129.4 | 44                 | 16.9  |
| 65      | 22                    | 110.5 | 50               | 103.4 | 44                 | 36.1  |

Silicone Glycereth

A specified number of grams of Silmer UME (Examples 20-22) are added to a specified amount of glycerin diesters (Examples 31-41) and/or glycerin monoesters (examples 23-30). The reaction mixture is heated to 160-180° C. Water is removed by vacuum during the reaction process. The reaction is monitored by the determination of acid value. The acid value will diminish as the reaction proceeds. The reaction is cooled once the acid value fails to change over an additional two hours at elevated temperature. The product is used without purification.

|         | Silicone Undecylenate |       | Glycerin Diester |       | Glycerin Monoester |       |
|---------|-----------------------|-------|------------------|-------|--------------------|-------|
| Example | Example               | Grams | Example          | Grams | Example            | Grams |
| 67      | 20                    | 59.0  | 33               | 191.0 | —                  | —     |
| 68      | 21                    | 33.4  | 34               | 216.6 | —                  | —     |
| 69      | 22                    | 41.1  | 35               | 208.9 | —                  | —     |
| 70      | 20                    | 56.5  | 36               | 193.5 | —                  | —     |
| 71      | 21                    | 81.3  | 37               | 168.7 | —                  | —     |
| 72      | 22                    | 72.2  | 38               | 177.8 | —                  | —     |
| 73      | 21                    | 41.3  | 33               | 183.9 | 27                 | 24.8  |
| 74      | 22                    | 49.7  | 34               | 183.1 | 28                 | 17.1  |
| 75      | 22                    | 56.2  | 34               | 155.1 | 28                 | 38.7  |
| 76      | 21                    | 33.2  | 35               | 178.8 | 29                 | 38.0  |
| 77      | 22                    | 46.8  | 36               | 167.2 | 30                 | 36.6  |
| 78      | 22                    | 47.9  | 36               | 128.3 | 30                 | 73.8  |
| 79      | 21                    | 83.5  | 37               | 129.9 | 31                 | 36.6  |
| 80      | 22                    | 69.1  | 38               | 136.1 | 32                 | 44.8  |
| 81      | 22                    | 66.3  | 38               | 97.9  | 32                 | 85.8  |

The polymers of the present invention are used without additional purification.

The compounds of the present invention have exceptional skin feel, providing moisturization, and a dry feel. Additionally, the compounds of the present invention are exceptionally mild to the eye and skin, making them outstanding candidates for personal care applications.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:
1. A polysilicone having the following structure;

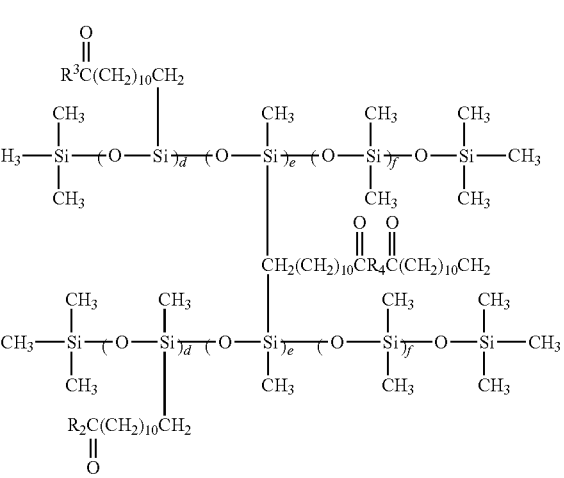

wherein;
d is an integer ranging from 1 to 10;
e is an integer ranging from 0 to 4;
f is an integer ranging from 0 to 20;
c is an integer ranging from 3 to 30, with the proviso that d +e +f =c;
$R^3$ is selected from the group consisting of:

$$\begin{array}{cc} CH_2OR^1 & CH_2OR^1 \\ | & | \\ CHOR^1 & CHOR^2 \\ | & | \\ CH_2O\text{---} , & CH_2O\text{---} \end{array}$$

and mixtures thereof;
wherein;
$R^1$ conforms to the following structure:

$$CH_3-\underset{\underset{CH_3}{|}}{\overset{\overset{CH_3}{|}}{Si}}-[(O-\underset{\underset{CH_3}{|}}{\overset{\overset{CH_3}{|}}{Si}})_a-(O-\underset{\underset{CH_3}{|}}{\overset{\overset{CH_3}{|}}{Si}})_b]_c-O-\underset{\underset{CH_3}{|}}{\overset{\overset{CH_3}{|}}{Si}}-CH_3$$
$$\underset{\underset{O}{\|}}{\text{---}C(CH_2)_{10}CH_2}$$

a is an integer ranging from 1 to 10;
b is an integer ranging from 0 to 20;
$R^2$ is alkyl containing 8 to 26 carbons;
$R^4$ conforms to the following structure:

$$\begin{array}{c} CH_2OC(O)R^5 \\ | \\ CHO\text{---} \\ | \\ CH_2O\text{---} \end{array}$$

wherein;
$R^5$ is selected from a group consisting of:

$$CH_3-\underset{\underset{CH_3}{|}}{\overset{\overset{CH_3}{|}}{Si}}-[(O-\underset{\underset{O=C(CH_2)_{11}}{|}}{\overset{\overset{CH_3}{|}}{Si}})_a-(O-\underset{\underset{CH_3}{|}}{\overset{\overset{CH_3}{|}}{Si}})_b]_c-O-\underset{\underset{CH_3}{|}}{\overset{\overset{CH_3}{|}}{Si}}-CH_3, \text{ and}$$

alkyl containing 8 to 26 carbons;
a is an integer ranging from 1 to 10;
b is an integer ranging from 0 to 20.

2. The polysilicone of claim 1 wherein a is 1.
3. The polysilicone of claim 1 wherein a is 5.
4. The polysilicone of claim 1 wherein x is 2.
5. A polysilicone having the following structure;

$$CH_3-\underset{\underset{CH_3}{|}}{\overset{\overset{CH_3}{|}}{Si}}-(O-\underset{\underset{R^3C(CH_2)_{10}}{|}\atop\underset{O}{\|}}{\overset{\overset{CH_3}{|}}{Si}})_a-(O-\underset{\underset{R^4C(CH_2)_{10}}{|}\atop\underset{O}{\|}}{\overset{\overset{CH_3}{|}}{Si}})_e-(O-\underset{\underset{CH_3}{|}}{\overset{\overset{CH_3}{|}}{Si}})_f-O-\underset{\underset{CH_3}{|}}{\overset{\overset{CH_3}{|}}{Si}}-CH_3$$

-continued $$CH_3-\underset{\underset{CH_3}{|}}{\overset{\overset{CH_3}{|}}{Si}}-(O-\underset{\underset{R^2C(CH_2)_{10}}{|}\atop\underset{O}{\|}}{\overset{\overset{CH_3}{|}}{Si}})_d-O-\underset{\underset{CH_3}{|}}{\overset{\overset{\overset{O}{\|}}{C(CH_2)_{10}}}{Si}})_e-(O-\underset{\underset{CH_3}{|}}{\overset{\overset{CH_3}{|}}{Si}})_f-O-\underset{\underset{CH_3}{|}}{\overset{\overset{CH_3}{|}}{Si}}-CH_3$$

wherein;
d is an integer ranging from 1 to 10;
e is an integer ranging from 0 to 4;
f is an integer ranging from 0 to 20;
c is an integer ranging from 3 to 30, with the proviso that d+e+f=c;
$R^2$ is alkyl containing 8 to 26 carbons;
$R^3$ is selected from the group consisting of:

$$\begin{array}{c} CH_2O(CH_2CH_2O)_xR^1, \\ | \\ CHO(CH_2CH_2O)_xR^1 \\ | \\ CH_2O\text{---} \\ CH_2O(CH_2CH_2O)_xR^1 \\ | \\ CHO(CH_2CH_2O)_xR^2 \\ | \\ CH_2O\text{---} \end{array}$$

and mixtures thereof;
wherein;
x is an integer ranging from 3 to 8;
$R^1$ is selected from a silicone polymer that has the following structure:

$$CH_3-\underset{\underset{CH_3}{|}}{\overset{\overset{CH_3}{|}}{Si}}-[(O-\underset{\underset{O=C(CH_2)_{11}}{|}}{\overset{\overset{CH_3}{|}}{Si}})_a-(O-\underset{\underset{CH_3}{|}}{\overset{\overset{CH_3}{|}}{Si}})_b]_c-O-\underset{\underset{CH_3}{|}}{\overset{\overset{CH_3}{|}}{Si}}-CH_3, \text{ and}$$

alkyl ranging from 8 to 26 carbons, or mixtures thereof, with the proviso that $R^1$ is different than $R^2$;
a is an integer ranging from 1 to 10;
b is an integer ranging from 0 to 20;
$R^4$ conforms to the following structure:

$$\begin{array}{c} CH_2O(CH_2CH_2O)_xR^5 \\ | \\ CHO(CH_2CH_2O)_x\text{---} \\ | \\ CH_2O(CH_2CH_2O)_x\text{---} \end{array}$$

wherein;
x is an integer ranging from 3 to 8;
$R^5$ is selected from a group consisting of:
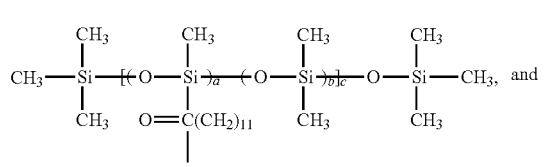 and
and
alkyl containing 8 to 26 carbons;
a is an integer ranging from 1 to 10;
b is an integer ranging from 0 to 20.
6. The polysilicone of claim 5 wherein a is 5.
7. The polysilicone of claim 5 wherein a is 8.
8. The polysilicone of claim 5 wherein x is 3.
9. The polysilicone of claim 5 wherein x is 8.
* * * * *